United States Patent [19]

Kandarpa et al.

[11] Patent Number: 5,323,778
[45] Date of Patent: Jun. 28, 1994

[54] METHOD AND APPARATUS FOR MAGNETIC RESONANCE IMAGING AND HEATING TISSUES

[75] Inventors: Krishna Kandarpa, Wayland; Peter Jakab, Sharon, both of Mass.

[73] Assignee: Brigham & Women's Hospital, Boston, Mass.

[21] Appl. No.: 786,879

[22] Filed: Nov. 5, 1991

[51] Int. Cl.$^5$ .............................................. A61B 5/055
[52] U.S. Cl. ................................ 128/653.2; 128/653.5; 606/28; 606/29; 607/101; 607/154; 607/113
[58] Field of Search ................ 128/653.2, 653.5, 736; 607/154, 113, 97, 101, 102; 606/28, 29, 31, 33–35, 41

[56] References Cited

U.S. PATENT DOCUMENTS

| | | |
|---|---|---|
| 4,254,778 | 3/1981 | Clow et al. . |
| 4,572,198 | 2/1986 | Codrington . |
| 4,648,405 | 3/1987 | Keren . |
| 4,672,972 | 6/1987 | Berke . |
| 4,813,429 | 3/1989 | Eshel et al. . |
| 4,823,812 | 4/1989 | Eshel et al. . |
| 4,831,330 | 5/1989 | Takahashi . |
| 4,832,023 | 5/1989 | Murphy-Chutorian et al. . |
| 4,858,613 | 8/1989 | Fry et al. ........................ 128/660.03 |
| 4,905,698 | 3/1990 | Strohl, Jr. et al. . |
| 4,917,097 | 4/1990 | Proudian et al. . |
| 4,932,411 | 6/1990 | Fritschy et al. . |
| 4,951,688 | 8/1990 | Keren ........................... 128/653.002 |
| 4,961,422 | 10/1990 | Marclosky et al. ................. 128/784 |
| 5,019,076 | 5/1991 | Yamanashi et al. ................. 606/45 |
| 5,109,853 | 5/1992 | Taicher et al. ................. 128/653.002 |
| 5,131,392 | 7/1992 | Jolesz et al. ................. 128/653.002 |
| 5,170,789 | 12/1992 | Narayan et al. ................. 128/653.5 |

*Primary Examiner*—Lee S. Cohen
*Assistant Examiner*—Brian L. Casler
*Attorney, Agent, or Firm*—Sterne, Kessler, Goldstein & Fox

[57] ABSTRACT

The present invention relates to apparatus and a method for imaging and heating body tissues with one probe, through use of a magnetic resonance imaging radio frequency source. The device may also be configured with a thermocouple to provide temperature-controlled heat therapy with sufficient image definition to control that therapy.

15 Claims, 4 Drawing Sheets

METHOD AND APPARATUS FOR MAGNETIC RESONANCE IMAGING AND HEATING TISSUES

FIELD OF THE INVENTION

The present invention relates to apparatus for imaging and heating body tissues. More particularly, the invention utilizes a probe containing a Magnetic Resonance Imaging (MRI) coil and heating apparatus to perform both imaging and therapy with one probe.

BACKGROUND OF THE INVENTION

Magnetic Resonance Imaging (MRI) apparatus is used in the medical field for diagnosis. Any object which is to be imaged by MRI apparatus must be placed within a spatially varying magnetic field and then subjected to a perturbation pulse of radio frequency (RF) radiation. An MRI imaging coil then detects the resulting nuclear magnetic resonance spectra which are combined to give cross-sectional images. When a patient is being "imaged" for medical diagnosis, a large electromagnetic coil which completely surrounds the patient is normally used. A separate imaging coil may be used on the skin surface of the patient to obtain improved resolution of the magnetic resonance image. In some MRI devices, one external coil is used for both excitation and reception, the two functions of the coil being interleaved in time.

Imaging tissues deep within the body with this system has two problems. First, the depth of the sample that can be imaged is approximately equal to the width of the imaging coil so the greater the depth to be imaged, the larger the imaging coil must be. Second, the signal-to-noise ratio will decrease with increased depth of the image so the resolution and image definition will also decrease with increased depth of the image. As a result, the resolution provided by conventional external imaging coils is not sufficient for controlling a therapy procedure. These problems can be overcome to a large degree by using an imaging coil that is placed within the body of the patient. With the imaging coil within the patient, it can be placed adjacent to the tissues of interest such that depth is no longer a limiting factor. The resolution and image definition for these tissues with an internal imaging coil will be much greater than that obtained with an external imaging coil.

A probe which provides the imaging from within the body is disclosed in U.S. Pat. No. 4,672,972 to Berke (the Berke patent). The Berke probe includes an imaging coil which may be tuned to an emission frequency of interest. The external processor for this probe may also excite the coil to radiate a localized perturbation field prior to obtaining the emission data of interest. The Berke probe is limited, however, to diagnostic functions and cannot perform any therapy functions.

Hyperthermia therapy can be accomplished using probes or applicators such as that disclosed in U.S. Pat. No. 4,823,812 to Eschel, et al. (the Eschel applicator). The Eschel applicator can be used for hyperthermia treatment by insertion into body cavities. The applicator includes a microwave antenna which generates radio frequency (RF) electromagnetic radiation for heating the body tissue. The Eschel applicator has no capability for imaging or locating the applicator within the patient's body.

One way to locate the applicator is through use of the catheter and probe disclosed in U.S. Pat. No. 4,813,429 to Eschel, et al. (the Eschel probe). The Eschel probe includes a diode for detection of the peak of the microwave field generated by the Eschel applicator. The Eschel applicator is then positioned until the peak is detected by the Eschel probe. The Eschel probe also contains thermocouples for measuring the heat produced by the Eschel applicator during the therapy. Therefore, to provide the hyperthermia therapy at the proper location requires use of both the Eschel applicator and the Eschel probe. No imaging of the surrounding tissues is achieved through use of these two devices.

A therapy device such as the Eschel applicator could also be used in conjunction with an alternative method of imaging for use in controlling the therapy procedure. Such alternatives include direct visual feedback (e.g., intraoperative cauterization), x-ray fluoroscopy, or ultrasound.

Accordingly, prior to the development of the present invention, no single device was capable of imaging the tissues for control of the therapy procedure, locating the therapy device in the correct location, and delivering the therapy. It is therefore an object of this invention to provide a probe which is capable of imaging tissues from within the body with sufficient resolution to control heat therapy, and which is capable of delivering the heat therapy. It is a further object to provide a probe with the capability for temperature monitoring of the heat therapy. It is an advantage of this invention that imaging and heat therapy can be performed using only the magnetic resonance imaging radio frequency source such that no independent RF source is required.

SUMMARY OF THE INVENTION

The present invention is a device which is capable of heat therapy and of imaging tissues with sufficient definition to control that therapy. The device of the present invention includes a probe which contains a magnetic resonance imaging coil that is used with a magnetic resonance imaging (MRI) radio frequency (RF) source to image the tissues. The imaging coil includes a coil body and a coil tip, and can be adjusted to select particular frequencies of interest (tuneable coil). A heating device which uses the same magnetic resonance imaging radio frequency source is included to perform the heat therapy. The heating device may ground the tissue eddy currents which are produced by the alteration of the magnetic field resulting from activation of the MRI radio frequency source. The heating device can include a wire pair, although only a single wire is necessary for heating, with the endoluminal end of the wire being welded together to form a heating tip.

In another aspect, the device of the present invention also includes a thermocouple to detect temperature. The wire pair of the heating device can serve as a temperature detector. By detecting temperature, the device of the present invention can provide heat therapy which is temperature controlled. One coaxial cable carries the thermocouple signal as well as the signal from the magnetic resonance imaging coil.

Furthermore, the present invention includes a method for using the device for imaging and heating of tissues which includes the steps of: introducing a catheter into the body to a location proximate to the tissues to be heated; imaging the tissues using the magnetic resonance imaging coil in the probe and the magnetic resonance imaging RF source; and heating the tissues using heating apparatus and the magnetic resonance imaging RF source. The imaging coil for this method can be adjusted to select particular frequencies of interest (tuneable coil). The heating device for this method may ground the tissue eddy currents which are produced by the alteration of the magnetic field resulting from activation of the MRI radio frequency source. The heating device for this method can include a wire pair with the endoluminal end of the wire being welded together to form a heating tip. The probe used in this method can further include a thermocouple to detect temperature.

The present invention also includes the method for imaging and heating of tissues which includes the steps of: introducing a catheter into the body to a location proximate to the tissues to be heated; imaging the tissues using the magnetic resonance imaging coil in the probe and the magnetic resonance imaging RF source; heating the tissues using heating apparatus and the magnetic resonance imaging RF source; and controlling the heating by use of the probe which contains a thermocouple to detect temperature. This method can be performed at a temperature sufficient to remove an obstruction or to create an occlusion. The imaging coil for this method can be adjusted to select particular frequencies of interest. The heating device for this method may ground the tissue eddy currents which are produced by the alteration of the magnetic field resulting from activation of the MRI radio frequency source. The heating device for this method can include a wire pair with the endoluminal end of the wire being welded together to form a heating tip.

BRIEF DESCRIPTION OF THE DRAWINGS

Various objects, features, and advantages of the present invention will be more fully appreciated as the same becomes better understood from the following detailed description of the present invention when considered in connection with the accompanying drawings, in which.

DETAILED DESCRIPTION OF THE DRAWINGS

Figure 1:
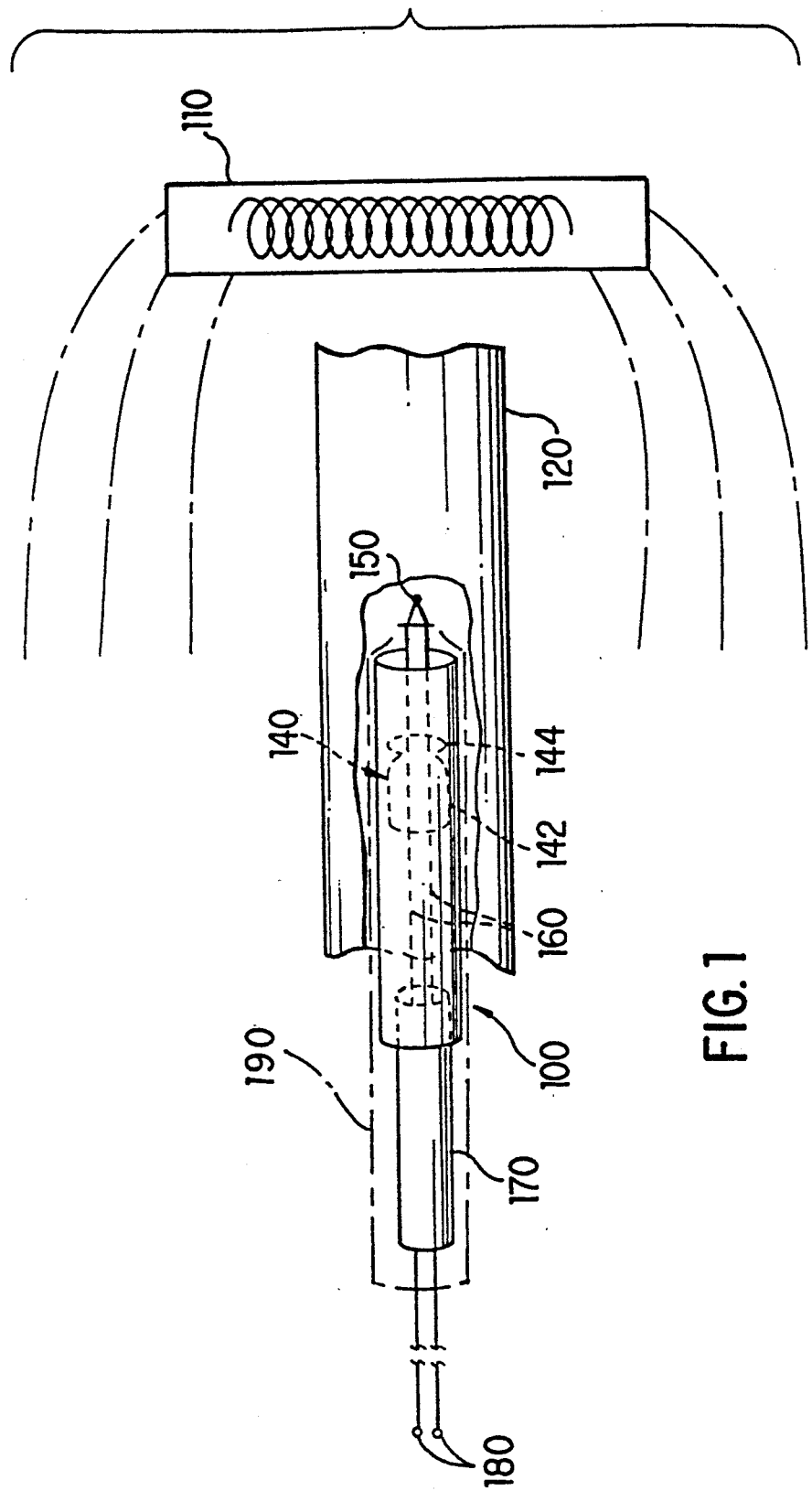
FIG. 1 is a longitudinal cross-sectional view of the probe inserted in an artery or other body passageway, with a magnetic resonance imaging radio frequency excitation coil external to the body.

With continuing reference to the drawing figures in which similar reference numerals are used throughout the description to describe similar features of the invention, the probe 100 is shown inserted in an artery or other body passageway 120 in FIG. 1. The probe contains the magnetic resonance imaging coil 140, which is comprised of an imaging coil body 142 and an imaging coil tip 144. The imaging coil works in conjunction with the magnetic resonance imaging RF source or excitation coil 110 to provide an image of the surrounding tissues from within the body. The RF source is shown here as external to the body of the patient, but could be located within the body. The probe further comprises RF heating apparatus which includes a wire pair 160, the wires of which are welded together at the endoluminal end of the probe to form a tip 150. The imaging signal is carried out of the probe by the coaxial cable 170, with access to the imaging coil signal at 180. The center conductor of coaxial cable 170 is a wire pair, with a shield and a ground.

Figure 2:
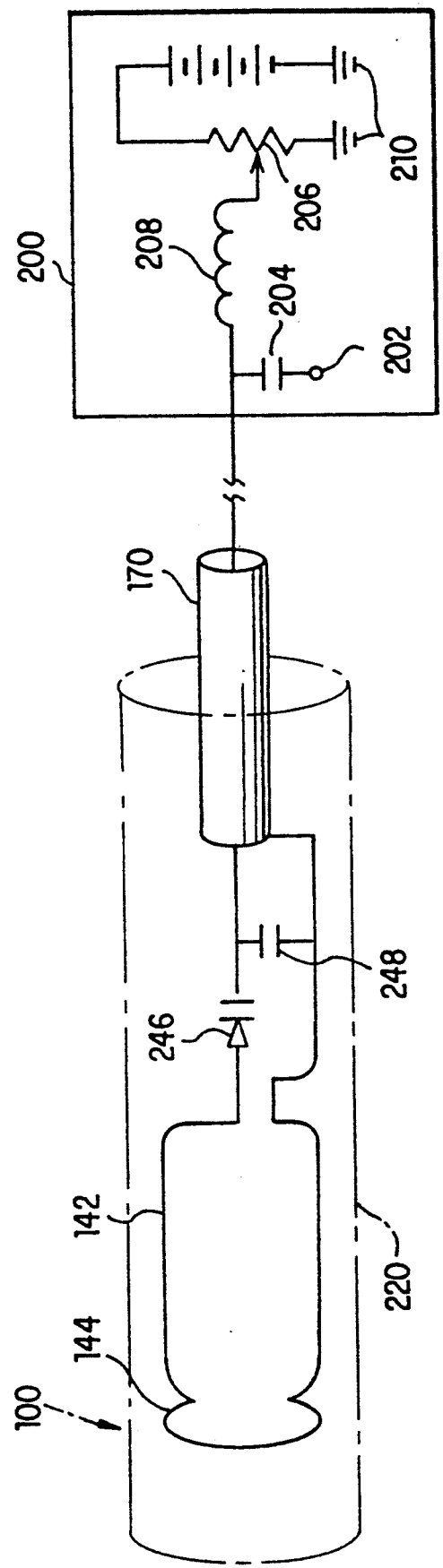
FIG. 2 is a cross-sectional view of the probe showing the magnetic resonance imaging coil and its connection to the coaxial cable, as well as the external coaxial cable filter circuit.

The imaging coil connecting circuitry can be seen in more detail in FIG. 2. To ensure stability of the coil, the winding and electrical components are encased in a plastic housing 220. The imaging coil itself comprises two parts, the imaging coil body 142 and the imaging coil tip 144, so that the imaging coil can be tuned to a frequency of interest. The tuning is accomplished via the imaging coil tuning capacitor 246. To provide tuning voltage for the voltage controlled tuning capacitor 246, the external end of coaxial cable 170 is connected to a filter circuit 200. In the filter circuit 200, the input 202 from the magnetic resonance imaging RF source preamplifier is connected via a direct current blocking capacitor 204 to the coaxial cable. A variable voltage source 206 is connected via a direct current bypass inductor 208 to the coaxial cable. The system ground 210 terminals of the variable voltage source 206 are connected together. The filter circuit 200 thus provides voltage for the tuning capacitor 246 which is filtered from the magnetic resonance imaging RF source.

The imaging coil of FIG. 2 is a receive-only coil, i.e., the coil does not radiate. The signal received by the imaging coil is carried by the double wire and the ground of the coaxial cable 170 and capacitor 248 impedance matches the imaging coil signal to the coaxial cable 170.

Figure 3:
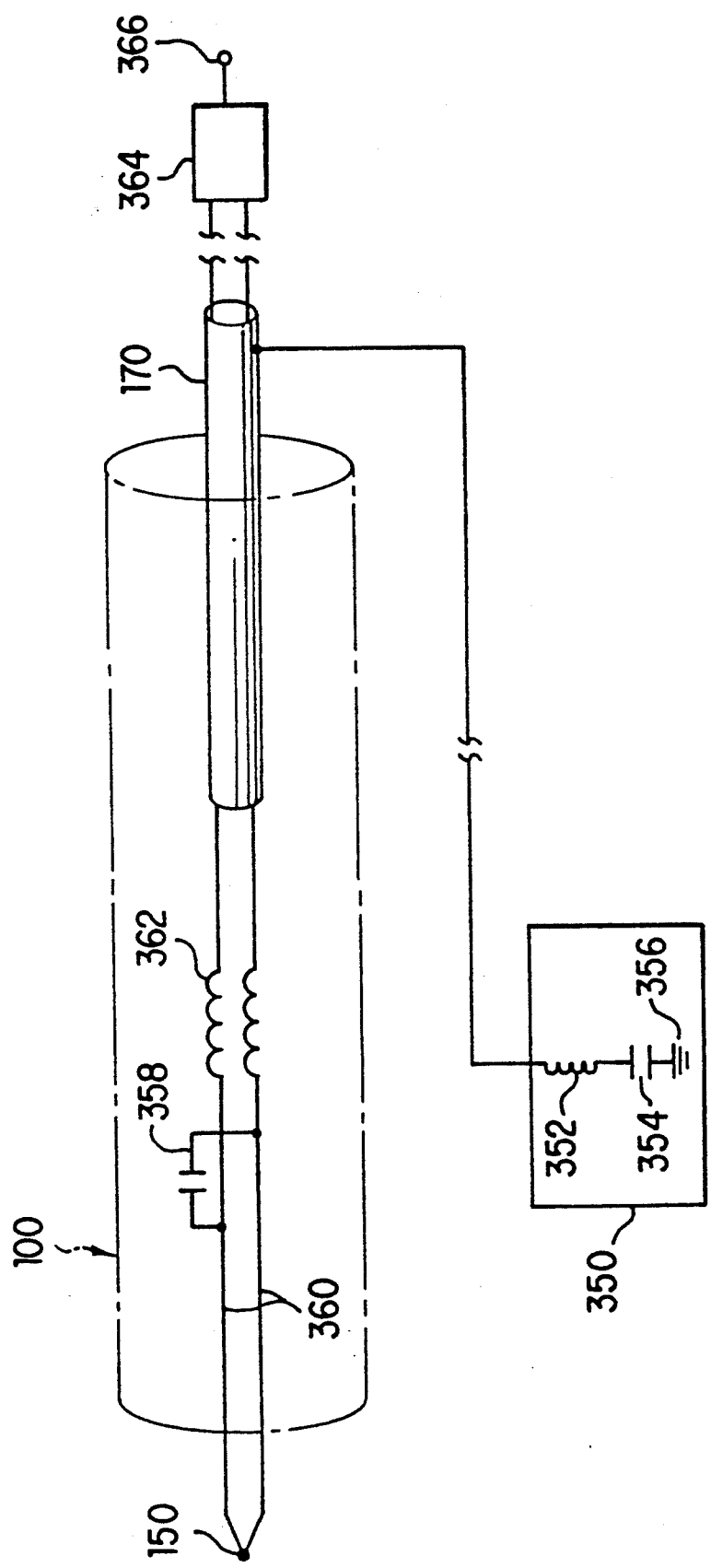
FIG. 3 is a cross-sectional view of the probe showing the radio frequency heating apparatus with the thermocouple wire pair.

FIG. 3 shows the probe 100 configured with RF heating apparatus including a thermocouple wire pair 360 and a heating tip 150 for performing heat therapy. The thermocouple wire pair 360 serves as a temperature sensor. The thermocouple signal is carried by the wire pair 360 and filtered from the RF signal by the double wound inductor 362. The thermocouple signal is carried by the double wire in the coaxial cable 170 in differential mode as the signal is determined by the voltage difference between the two wires. The coaxial cable is then connected to the thermocouple signal processing unit 364 from which the thermocouple signal output 366 can be accessed for procedure control.

The heat therapy is performed with the probe of FIG. 3 through use of the RF heating apparatus. To form the RF heating apparatus, the endoluminal end of the thermocouple wire pair 360 is welded to form the heating tip 150. When the RF source is activated, the alteration of the magnetic field of the surrounding tissues produces heat-generating eddy currents within the tissue. The RF heating apparatus grounds the tissue eddy currents and itself becomes heated.

The thermocouple wire pair 360 will form a low impedance point at a given frequency when the electrical path from a ground point is a multiple of the corresponding half wavelength. Therefore, the electrical path which forms the RF heating apparatus can be electrically tuned to correspond to the radio frequency used for excitation in order to properly ground the tissue eddy currents and generate heat. The electrical path can be tuned for use by the RF heating apparatus by the use of the tuning circuit 350 which is connected to the shield of the coaxial cable 170 as shown in FIG. 3. The tuning circuit 350 comprises a series connected inductor 352 and capacitor 354, one of which is tuneable. To close the RF circuit, the tuning circuit connects one or both conductors of the thermocouple wire pair to the system ground 356. When both conductors of the wire pair are used, a capacitor 358 connects them together.

The method of heating used by the probe in FIG. 3 requires an RF source or excitation coil to excite the tissues in interest, resulting in eddy currents being generated in those tissues. The tissues are then heated directly by the eddy currents. By grounding the eddy currents, additional heat is generated in the apparatus used for grounding. In the preferred embodiment, the RF source is the same RF source used by the magnetic resonance imaging coil for imaging the tissues. As illustrated in FIG. 1, only one RF source is required, and the RF source is external to the body of the patient. The one MRI RF source provides the RF required by the magnetic resonance imaging coil and the RF required to generate heating for therapy. The MRI RF source is not restricted in location to being external to the body of the patient. Alternatively, an additional RF source may be used to generate the RF required for the heating. This invention could also be used with other means for heating, such as resistive heating, which are commonly used in probes for hyperthermia treatment.

Figure 4:
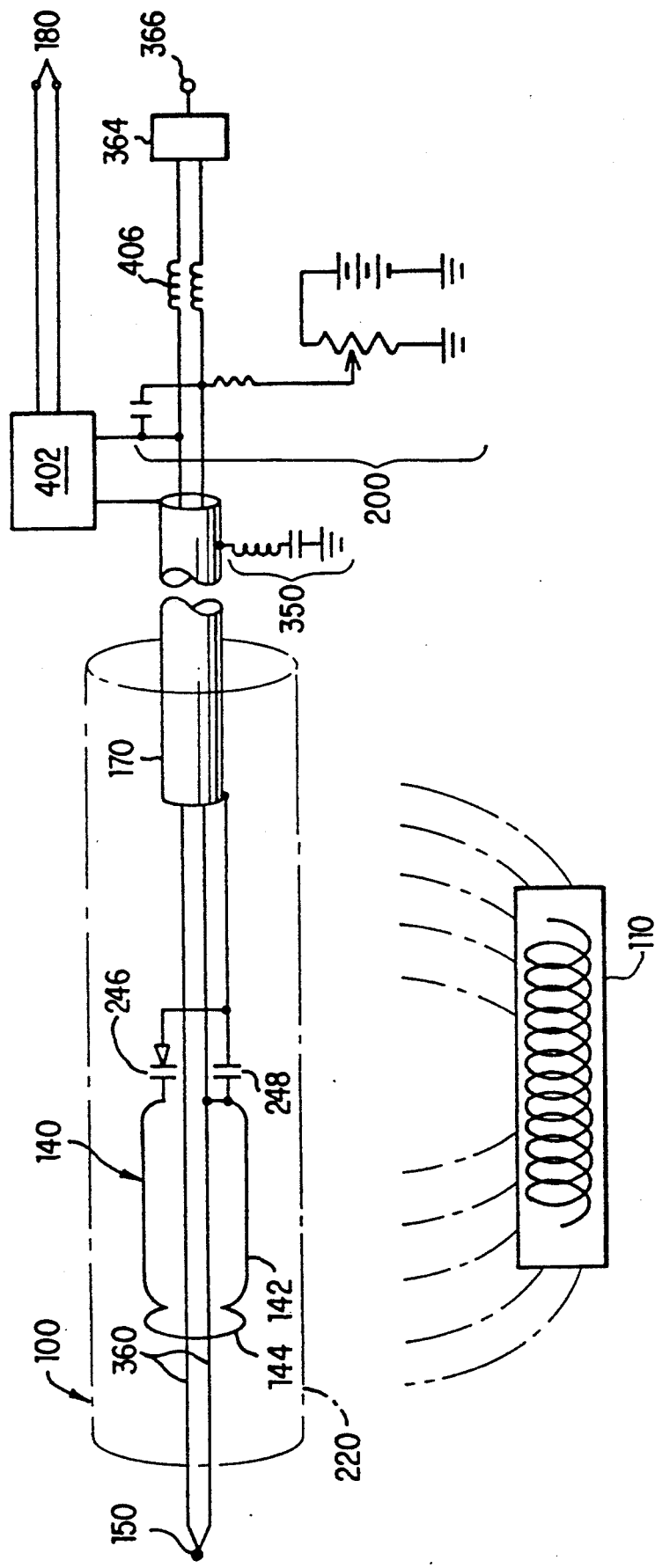
FIG. 4 is a cross-sectional view of the probe containing the magnetic resonance imaging coil, radio frequency heating apparatus with the thermocouple wire pair, and the external coaxial cable connections.

FIG. 4 shows the preferred configuration of a combined probe which includes a magnetic resonance imaging coil 140, and apparatus for RF heating and temperature measurement. The external magnetic resonance imaging RF source 110 provides the perturbation pulse of RF radiation which is used in conjunction with the imaging coil 140 to image the tissues for diagnosis and control of the heat therapy. The same source is used to provide the RF excitation which results in the tissue eddy currents which are then grounded to generate heat at the RF heating tip 150. The imaging coil comprises two parts, the imaging coil body 142 and the imaging coil tip 144, and is tuneable to a frequency of interest through the voltage controlled tuning capacitor 246 which is supplied by the variable voltage source in the filter circuit 200. The imaging coil signal is carried by the double wire and the ground of the coaxial cable 170. Impedance matching is accomplished via the imaging coil signal impedance matching capacitor 248. Impedance transforming of the coaxial cable is accomplished by switch 402 to separate out the imaging coil signal and provide access to the signal at 180.

Heating is achieved through use of the MRI RF source 110 which generates tissue eddy currents. The eddy currents are grounded by the thermocouple wire pair, the ends of which are welded to form the RF heating tip 150 which provides additional heating of the tissues. The electrical length of the thermocouple wire pair is adjusted by the tuning circuit 350 with the RF signal being carried by the shield of the coaxial cable 170. The thermocouple signal is carried in differential mode by the double wire in the coaxial cable. A thermocouple bypassing filter 406 separates the thermocouple signal for input into the thermocouple signal processing unit 364, with thermocouple signal access at 366 for procedure control.

Inside the probe, the thermocouple wire pair 360 carries both the thermocouple signal and the RF signal. As shown in FIG. 3, an inductor 362 can be used to filter the thermocouple signal from the RF signal. The coaxial cable 170 connects the probe to the external processing circuitry. The double wires within the coaxial cable carry the thermocouple signal in differential mode. That is, the signal is carried as a voltage difference between two wires. The magnetic resonance imaging coil signal is in a different frequency band from the thermocouple signal. Therefore, the double wire and the ground of the coaxial cable can also carry the imaging coil signal. The shield of the coaxial cable carries the RF energy which is grounded by the thermocouple wire pair to generate heat. Due to the multiple functions performed by the coaxial cable, these functions are interleaved in time. To prevent distortion to the magnetic resonance image, the voltage controlled tuning capacitor 246 detunes the imaging coil during RF excitation of the MRI RF source.

The device of the present invention can be used for diagnostic as well as treatment purposes and in its preferred embodiment, it is used for delivery of temperature-controlled heat therapy. To use the device of the present invention, a catheter 190 is introduced into a body passageway 120 proximate to the tissues which require the heat therapy, as shown in FIG. 1. The probe containing the magnetic resonance imaging coil, RF heating apparatus, and thermocouple is contained within the catheter. A commercially available Magnetic Resonance Imaging System, such as the General Electric 1.5 Tesla system, is used to provide the external RF source. The RF source and imaging coil are then used to image the tissues in interest. The external RF source also provides the field which generates tissue eddy currents which are grounded by the probe, resulting in the heating of the probe tip. The heat therapy is then performed with the probe, with the magnetic resonance images used for controlling the heat therapy procedure. The thermocouple wire pair detects the resulting temperature, thus providing temperature control for the therapy procedure. The therapies that can be performed include hyperthermia treatment as is done for prostate cancer or for hemorrhoids. Additionally, the probe can be used to provide a heating profile which results in the removal of an intraluminal occlusion or obstruction, such as in a blood vessel, or a heating profile which results in the creation of an occlusion. The probe of the present invention can also be used for diagnostic imaging without heat therapy.

The invention which is intended to be protected herein should not be construed as limited to the particular forms disclosed, as these are to be regarded as illustrative rather than restrictive. For example, the magnetic resonance imaging RF source need not be external to the probe, or external to the patient. The magnetic resonance imaging coil used in the device of the present invention need not be a receive-only coil, and the coil could be configured to radiate a localized perturbation field prior to receiving the tissue emission spectra. Additionally, other means for heating the tissues commonly used in hyperthermia treatment probes could be used with this invention.

Variations and changes may be made by those skilled in the art without departing from the spirit of the invention. Accordingly, the foregoing detailed description should be considered exemplary in nature and not limited to the scope and spirit of the invention as set forth in the following claims.

What is claimed is:

1. Apparatus for magnetic resonance imaging and heating of tissues, comprising:
   means for imaging including a magnetic resonance imaging radio frequency radiation source;
   a probe comprising a magnetic resonance imaging coil, said imaging coil receiving an emission spectra from said tissues produced by radiation from said magnetic resonance imaging radio frequency radiation source thereby producing a signal representing an image of said tissues;

means for heating said tissues disposed at lest partially within said probe, wherein said heating means uses said radiation to generate heat, and wherein said means for heating said tissues comprises a wire pair such that said wire pair contains a first end with said first end of said wire pair being welded; and signal output means for transmitting said signal out of said probe.

2. Apparatus according to claim 1, wherein said probe further comprises a thermocouple to detect temperature.

3. Apparatus for magnetic resonance imaging and heating of tissues, comprising:

means for imaging including a magnetic resonance imaging radio frequency radiation source;

a catheter comprising a probe wherein said probe comprises a magnetic resonance imaging coil, said imaging coil receiving an emission spectra from said tissues produced by radiation from said magnetic resonance imaging radio frequency radiation source producing a signal representing an image of said tissues, and a thermocouple to detect temperature;

signal output means for transmitting said signal out of said catheter;

and means for heating said tissues wherein said heating means uses said radiation to generate heat.

4. Apparatus according to claim 3, wherein said means for heating said tissues comprises means for grounding tissue eddy currents induced by radiation from said magnetic resonance imaging radio frequency radiation source.

5. Apparatus according to claim 3, further comprising a coaxial cable disposed at lest partially within said probe such that said imaging coil produces a signal which is impedance matched for carrying by said coaxial cable and, wherein said thermocouple produces a signal for carrying by said coaxial cable.

6. Apparatus according to claim 3, wherein said means for heating further comprises means for controlling said heating by detecting temperature.

7. Method for magnetic resonance imaging and heating of tissues, comprising the steps of:

introducing a catheter into a body to a location proximate to the tissues to be heated;

imaging said tissues using a means for imaging which includes a magnetic resonance imaging radio frequency radiation source and a probe contained within said catheter, said probe comprising a magnetic resonance imaging coil, said imaging coil receiving an emission spectra from said tissues produced by radiation from said magnetic resonance imaging radio frequency radiation source thereby producing a signal representing an image of said tissues;

transmitting said signal out of said catheter using signal output means;

heating said tissues with heating means, wherein said heating means uses said radiation to generate heat; and controlling said heating step by use of said probe, wherein said probe further comprises a thermocouple to detect temperature.

8. Method according to claim 7, wherein said heating step is performed with mans for grounding tissue eddy currents induced by said radiation.

9. Method according to claim 7, further comprising the step of: selecting the frequency of operation of said imaging coil, said imaging coil being adjustable over a multiplicity of frequencies.

10. Method according to claim 7, wherein said heating step is performed with heating means which comprises a wire pair such that said wire pair contains a first end with said first end of said wire pair being welded.

11. Method for magnetic resonance imaging and heating of tissues, comprising the steps of:

introducing a catheter into a body to a location proximate to the tissues to be heated;

imaging said tissues using a means for imaging which includes a magnetic resonance imaging radio frequency radiation source and a probe contained within said catheter, said probe comprising a magnetic resonance imaging coil, said imaging coil receiving an emission spectra from said tissues produced by radiation from said magnetic resonance imaging radio frequency radiation source thereby producing a signal representing an image of said tissues;

transmitting said signal out of said catheter using signal output means;

heating said tissues with heating means, wherein said heating means uses said radiation to generate heat, wherein said heating step is performed at a temperature sufficient to create an occlusion.

12. Method for magnetic resonance imaging and heating of tissues, comprising the steps of:

introducing a catheter into a body to a location proximate to the tissues to be heated;

imaging said tissues using a means for imaging which includes a magnetic resonance imaging radio frequency radiation source and a probe contained within said catheter, said probe comprising a magnetic resonance imaging coil, said imaging coil receiving an emission spectra from said tissues produced by radiation from said magnetic resonance imaging radio frequency radiation source thereby producing a signal representing an image of said tissues;

transmitting said signal out of said catheter using signal output means;

heating said tissues with heating means, wherein said heating means uses said radiation to generate heat; and detecting temperature with a thermocouple disposed within said probe.

13. Method for magnetic resonance imaging and heating of tissues, comprising the steps of:

introducing a catheter into a body to a location proximate to the tissues to be heated;

imaging said tissues using a means for imaging which includes a magnetic resonance imaging radio frequency radiation source and a probe contained within said catheter, said probe comprising a magnetic resonance imaging coil, said imaging coil receiving an emission spectra from said tissues produced by radiation from said magnetic resonance imaging radio frequency radiation source thereby producing a signal representing an image of said tissues;

transmitting said signal out of said catheter using signal output means;

heating said tissues with heating means, wherein said heating means uses said radiation to generate heat, wherein said heating step is performed with heating means which comprises a wire pair such that said wire pair contains a first end with said first end of said wire pair being welded.

14. Method according to claim 13, further comprising the step of:

detecting temperature with a thermocouple disposed within said probe.

15. Method for magnetic resonance imaging and heating of tissues, comprising the steps of:

introducing a catheter into a body to a location proximate to the tissues to be heated;

imaging said tissues using a means for imaging which includes a magnetic resonance imaging radio frequency radiation source and a probe contained within said catheter, said probe comprising a magnetic resonance imaging coil, said imaging coil receiving an emission spectra from said tissues produced by radiation from said magnetic resonance imaging radio frequency radiation source thereby producing a signal representing an image of said tissues;

transmitting said signal out of said catheter using signal output means;

heating said tissues with heating means, wherein said heating means uses said radiation to generate heat, wherein said heating step is performed with means for grounding tissue eddy currents induced by said magnetic resonance imaging radio frequency radiation.

* * * * *